(12) United States Patent
Qi et al.

(10) Patent No.: US 11,208,417 B2
(45) Date of Patent: Dec. 28, 2021

(54) SIMPLE PROCESS FOR PREPARING AVIBACTAM

(71) Applicant: XINFA PHARMACEUTICAL CO., LTD, Dongying (CN)

(72) Inventors: Yuxin Qi, Dongying (CN); Baolin Wang, Dongying (CN); Xin Xu, Dongying (CN); Lizhu Ju, Dongying (CN); Xinfa Li, Dongying (CN)

(73) Assignee: XINFA PHARMACEUTICAL CO., LTD, Shandong (CN)

( * ) Notice: Subject to any disclaimer, the term of this patent is extended or adjusted under 35 U.S.C. 154(b) by 417 days.

(21) Appl. No.: 16/345,791

(22) PCT Filed: Mar. 6, 2018

(86) PCT No.: PCT/CN2018/078073
§ 371 (c)(1),
(2) Date: Apr. 29, 2019

(87) PCT Pub. No.: WO2019/127903
PCT Pub. Date: Jul. 4, 2019

(65) Prior Publication Data
US 2021/0332060 A1 Oct. 28, 2021

(30) Foreign Application Priority Data
Dec. 25, 2017 (CN) .......................... 201711418424.X (51) Int. Cl.
*C07D 487/08* (2006.01)

(52) U.S. Cl.
CPC .................. *C07D 487/08* (2013.01)

(58) Field of Classification Search
CPC .......................... C07D 471/08; C07D 487/08
See application file for complete search history.

(56) References Cited

U.S. PATENT DOCUMENTS

| | | | |
|---|---|---|---|
| 8,829,191 B2* | 9/2014 | Ronsheim | A61P 43/00 546/121 |
| 10,570,132 B2* | 2/2020 | Qi | C07D 211/60 |
| 10,570,133 B2* | 2/2020 | Qi | C07D 211/60 |
| 10,662,190 B2* | 5/2020 | Wang | C07D 471/08 |

* cited by examiner

*Primary Examiner* — Deepak R Rao
(74) *Attorney, Agent, or Firm* — CBM Patent Consulting, LLC (57) ABSTRACT

The present invention provides a simple process of preparing avibactam. Piperidine-5-one-2S-carboxylate II as the raw material is subjected to condensation reaction with O-protecting hydroxylamine hydrochloride; the resulting compound is subjected to reduction and chiral resolution to obtain 5R-substituted oxyaminopiperidine-2S-carboxylic acid V in a basic condition; then, the compound of formula V is subjected to urea cyclization, acyl chlorination, and amidation with phosgene, solid phosgene, or diphosgene in a "one-pot" process, and then subjected to deprotection, sulfation, and tetrabutylammonium salt formation reaction to obtain (2S,5R)-2-carbamoyl-7-oxo-1,6-diazabicyclo[3.2.1]octan-6-yl]oxy}sulfonyl tetra-n-butyl ammonium salt VII, and finally, the compound of formula VII is subjected to ion exchange to obtain avibactam I.

10 Claims, 6 Drawing Sheets

SIMPLE PROCESS FOR PREPARING AVIBACTAM

FIELD

The present invention relates to the field of pharmaceutical biochemical engineering, and more particularly relates to a simple process for preparing avibactam.

BACKGROUND

As a non-β-lactam inhibitor, one of diazabicyclooctanone compounds, avibactam (I) may inhibit type A (including ESBL and KPC) and type C β-lactamases. When administered in combination with various types of cephalosporins and carbapenem antibiotics, avibactam has a broad spectrum activity against bacteria, particularly has a significant activity against *Escherichia coli* and *Klebsiella pneumoniae* containing ultra-broad spectrum β-lactamases, *Escherichia coli* containing excessive AmpC enzyme, and *Escherichia coli* containing both AmpC and ultra-broad spectrum β-lactamases. Avibactam (I), with the CAS No. 1192491-61-4 and the chemical name of [(1R,2S,5R)-2-(aminocarbonyl)-7-oxo-1,6-diazabicyclo[3.2.1]octan-6-yl] sodium sulphate, has a structural formula represented in Formula I:

Existing technologies for avibactam synthesis mainly involve two intermediates, i.e., intermediate VII: (2S,5R)-6-benzyloxy-7-oxo-1,6-diazabicyclo [3.2.1] octane-2-carboxamide; and intermediate VIII: 5R-[(benzyloxy) amino] piperidine-2S-carboxylate oxalate.

In the prior art, the patent literatures CN103649051A, CN105294690A, CN106866668A, WO2012086241, U.S. Pat. Nos. 8,148,540, 9,284,273, and 9,567,335, avibactam (I) was prepared from (2S,5R)-6-benzyloxy-7-oxo-1,6-diazabicyclo[3.2.1] octane-2-carboxamide (VII) as an intermediate. Compound VII was debenzylated under palladium-on-carbon catalyzation in the presence of different reducing agents (such as hydrogen, triethylsilane, sodium formate, and hydrazine hydrate), then sulfated by sulfur trioxide complex and salinized into quaternized ammonium, followed by ion exchange to obtain avibactam (I), as shown in Scheme 1.

Scheme 1

The intermediate product (2S,5R)-6-hydroxy-7-oxo-1,6-diazabicyclo[3.2.1] octane-2-carboxamide produced by debenzylation under hydrolysis according to this method has a poor stability and is prone to causing catalyst poisoning; besides, it needs a large amount of palladium-on-carbon catalyst (10% of the substrate concentration), which does not facilitate reduction of costs and has a poor industrial operability.

I. Synthesis of the Intermediate (2S,5R)-6-benzyloxy-7-oxo-1,6-diazabicyclo[3.2.1] octane-2-carboxamide (VII)

In the literatures above, the various processes of preparing the intermediate (2S,5R)-6-benzyloxy-7-oxo-1,6-diazabicyclo[3.2.1]octane-2-carboxamide (VII) are mainly divided into two schemes: amidation followed by urea cyclization; and urea cyclization followed by amidation, as shown in Scheme 2:

Scheme 2

The patents CN103649051A and CN105294690A adopted the scheme of amidation followed by urea cyclization. 5R-[(benzyloxy)amino] piperidine-2S-carboxylate oxalate (VIII) as the raw material was amidated in a methanol solution of ammonia gas or an alcohol solution of ammonia and the reaction mixture was filtered to remove ammonium oxalate; the ammonium oxalate filter cake was washed with methanol and the resulting methanol solution was concentrated; the product was extracted with methylbenzene and recrystallized with an appropriate solvent to obtain (2S,5R)-5-[(benzyloxy)amino]piperidine-2-carboxamide (yield: 68-99%); then, the amino on the piperidine ring of the resulting (2S, 5R)-5-[(benzyloxy)amino] piperidine-2-carboxamide was protected with 9-fluorenylmethyl chloroformate (FMOC-Cl) and a carbonylation reaction between carbonyl diimidazole and benzyloxylamine was carried out; and after the removal of the protection group on the piperidine ring by diethylamine, urea cyclization was carried out to obtain (2S,5R)-6-benzyloxy-7-oxo-1,6-diazabicyclo[3.2.1]octane-2-carboxamide (yield: 90%, total yield: 61.2-89.1%). In that preparation process, the post-amidation treatment is complicated; and the protecting agent 9-fluorenylmethyl chloroformate used for urea cyclization was expensive. Besides, the 9-fluorenylmethyl chloroformate and the carbonyl diimidazole only provided one carbonyl, such that the reaction had a poor atom economy, which does not facilitate environment protection and cost reduction. Further, direct urea cyclization of (2S, 5R)-5-[(benzyloxy) amino] piperidine-2-carboxamide using triphosgene and carbonyl diimidazole without protection of the amino on the piperidine ring had a low yield (50-56%) without industrial value.

Further, the patents CN102834395A, CN103649051A, CN103328476A, CN106279163A, CN106565712A, U.S. Pat. Nos. 9,284,273, and 9,567,335 all involve a process of urea cyclization followed by amidation. 5R-[(benzyloxy) amino] piperidine-2S-carboxylate oxalate (VIII) as the raw material was urea cyclized using triphosgene-organic base, carbonyl diimidazole or other carbonylation agents, then hydrolyzed in an alkaline condition such as the aqueous lithium hydroxide to obtain (2S,5R)-6-benzyloxy-7-oxo-1, 6-diazabicyclo[3.2.1]octane-2-carboxylic acid; then, the carboxyl was activated into anhydride using trimethylacetyl chloride or other agents and then the anhydride was amidated using the aqueous ammonia to obtain (2S,5R)-6-benzyloxy-7-oxo-1,6-diazabicyclo[3.2.1]octane-2-carboxamide (VII), with a total yield of 34.5-65.5%. (2S,5R)-6-benzyloxy-7-oxo-1,6-diazabicyclo[3.2.1]octane-2-carboxylate obtained by urea-cyclization had a low reactivity, which could not be directly amidated in a methanol solution of ammonia gas. Instead, to be effectively amidated, the ester group needed to be hydrolyzed into the carboxyl, and then the carboxyl was activated into the anhydride. This process had a complicated operation procedure and a poor atom economy, which thus did not facilitate environment protection and industrial production.

II. Synthesis of the Intermediate 5R-[(benzyloxy) amino] piperidine-2S-carboxylate oxalate (VIII)

The U.S. patents US2010197928 and US2013012712 disclose a synthesis of 5R-[(benzyloxy)amino]piperidine-2S-carboxylate oxalate (VIII) (see Scheme 3). Briefly, the N-protected L-pyroglutamate as the starting material was ring-opened with trimethyl sulfoxide iodide to extend the carbon chain, the carbonyl of it was converted to imine by benzyloxyamine, and then the intermediate was deprotected under an acidic condition, cyclized under a basic condition, and finally reduced by a reducing agent and subjected to chiral resolution to obtain a product 5R-[(benzyloxy)amino] piperidine-2S-carboxylate oxalate. The starting materials, N-protected L-pyroglutamate, trimethyl sulfoxide iodide, methanesulfonic acid, used in this process were expensive; with dimethylsulfoxide as the solvent, a large amount of waste water was produced, such that it was not environment friendly; besides, the total yield was low (59%).

Scheme 3

The U.S. Patent Application No. US20140275001 discloses another synthesis process of 5R-[(benzyloxy)amino] piperidine-2S-carboxylate (free form of VIII) (scheme 4), wherein the N-protected L-pyroglutamate was still utilized as the starting material and was ring-opened with trimethyl sulfoxide iodide to extend the carbon chain. The difference lies in that in the patent US20140275001, the cyclization was firstly carried out by an iridium catalyst to obtain an alcohol with S-conformation through chiral reduction of the carbonyl; and then inversion of the SN2 configuration was realized by using N-benzyloxy-2-nitrobenzenesulfonamide and hydroxyl was converted into amino; 2-nitrobenzenesulfonyl chloro group was first removed under the action of lithium hydroxide and mercaptoacetic acid, and then the N-protecting group was removed by trifluoroacetic acid to obtain the free form of the product VIII. The process had a complicated operation and used the expensive iridium catalyst and the special odorous mercaptoacetic acid; besides, it produced a large amount of waste water, but the total yield was only 15%.

Scheme 4

In view of the above, the synthesis schemes including intermediate 5R-[(benzyloxy)amino]piperidine-2S-carboxylate oxalate (VIII) and the intermediate (2S,5R)-6-benzyloxy-7-oxo-1,6-diazabicyclo[3.2.1]octane-2-carboxamide (VII) for synthesizing avibactam are long and use expensive starting materials; they need a great amount of expensive palladium-on-carbon catalyst; further, they discharge a large amount of waste water, waste gas, and waste residuals, which are not environment-friendly and have a low atomic economy. Additionally, the complicated operations do not facilitate industrial production.

SUMMARY

To solve the drawbacks in the prior art, the present invention provides a simple process for preparing avibactam. The present invention has simple preparing steps, simple schemes, ease of operation, and inexpensive starting materials; besides, the present invention does not need the expensive palladium-on-carbon catalyst, such that it has a low cost; further, it discharges less waste water, waste gas, and waste residuals, such that it is environment friendly; the yields of its respective steps are high, which facilitate industrial production of avibactam.

Definition of Terms

Compound of Formula II: piperidine-5-one-2S-carboxylate.

Compound of Formula III: 5-substituted oxyiminopiperidine-2S-carboxylate, where the curve in the structural formula represents a mixture of two chiral structures.

Compound of Formula IV: 5R-substituted oxyaminopiperidine-2S-carboxylate oxalate.

Compound of Formula V: 5R-substituted oxyaminopiperidine-2S-carboxylic acid.

Compound of Formula VI: (2S,5R)-6-substituted oxy-7-oxo-1,6-diazabicyclo [3.2.1] octane-2-carboxamide.

Compound of Formula VII: (2S,5R)-2-carbamoyl-7-oxo-1,6-diazabicyclo[3.2.1]octan-6-yl]oxy}sulfonyl tetra-n-butyl ammonium salt; in the structure, -Bu refers to n-butyl.

The numbering of the compounds in the specification is completely consistent with the numbering of their structural formulae, and they have the same references.

The technical solution of the present invention is provided below.

A process for preparing avibactam comprises steps of:

(1) a compound of formula II and O-protecting hydroxylamine hydrochloride are subjected to condensation reaction in solvent a and under the catalysis of base a to prepare a compound of formula III:

where R in the compound of formula II is identical to R in the compound of formula III, which is one selected from the group consisting of methyl, ethyl, isopropyl, n-propyl, tert-butyl, n-butyl, isobutyl, or benzyl; PG in the compound of formula III is one selected from the group consisting of methoxymethyl, benzyloxymethyl, tert-butyldimethylsilyl, tert-butyldiphenylsilyl, triethylsilyl or triisopropylsilyl;

(2) the compound of formula III is subjected to reduction with a reducing agent in the presence of concentrated sulphuric acid and ethyl acetate and chiral resolution to obtain the compound of Formula IV where R and PG in the compound of the formula IV have the same meanings as R and PG in the compound of formula III;

(3) the compound of formula IV is hydrolyzed in the presence of base b and in solvent b to obtain the compound of formula V;

where PG in the compound of the formula V has the same meaning as PG in the compound of formula IV;

(4) the compound of formula V is subjected to urea cyclization and acyl chlorination with phosgene, solid phosgene or diphosgene in the presence of base c and catalyst and in solvent c, and then is subjected to amidation to obtain the compound of formula VI;

where PG in the compound of the formula VI has the same meaning as PG in the compound of formula V;

(5) the compound of the formula VI is subjected to deprotection with a deprotection reagent, sulfation, and tetrabutylammonium salt formation under the catalysis of base d and in solvent d to obtain the compound of VII;

(6) the compound of the formula VII is subjected to ion exchange to obtain avibactam (I).

Preferably according to the present disclosure, in step (1), the O-protecting hydroxylamine hydrochloride is one selected from the group consisting of methoxymethylhydroxylamine hydrochloride, benzyloxymethylhydroxylamine hydrochloride, tert-butyldimethylsilyl hydroxylamine hydrochloride, tert-butyldiphenylsilylhydroxylamine hydrochloride, triethylsilylhydroxylamine hydrochloride, triisopropylsilylhydroxylamine hydrochloride; a molar ratio between the O-protecting hydroxylamine hydrochloride and the compound of formula II is 0.9~1.5:1.

Preferably, according to the present invention, in step (1), solvent a is one selected from the group consisting of methanol, ethanol, propanol, butanol, ethyl acetate, tetrahydrofuran, acetonitrile, dichloromethane, chloroform, 1,2- dichloroethane, benzene, and toluene, or a mixture of two or more thereof; a mass ratio between solvent a and the compound of formula II is 3~15:1; and preferably, a mass ratio between solvent a and the compound of formula II is 6~10:1.

Preferably, according to the present invention, in step (1), base a is an inorganic base or an organic base; preferably, the inorganic base is selected from the group consisting of potassium carbonate, sodium carbonate, calcium carbonate, potassium hydrogencarbonate, sodium hydrogencarbonate, calcium hydrogencarbonate, potassium acetate, sodium acetate or calcium acetate, or a combination of two or more thereof, and the organic base is selected from the group consisting of triethylamine or tri-n-butylamine, or a combination of two thereof; a mass ratio between base a and the compound of formula II is 0.5~1.5:1.

Preferably according to the present disclosure, in step (1), the temperature for the condensation reaction ranges from 30° C. to 80° C.; preferably, the temperature for the condensation reaction ranges from 30° C. to 60° C. A duration for the condensation reaction ranges from 2 hours to 5 hours.

Preferably, according to the present disclosure, in step (2), the concentrated sulfuric acid is a sulfuric acid with a mass fraction ranging from 95% to 98%, and the molar ratio between the concentrated sulfuric acid and the compound of the formula III is (3.0~6.0):1; preferably, the concentrated sulfuric acid is a sulfuric acid with a mass fraction of 98%. The present invention adopts a method of combining the concentrated sulfuric acid and the substrate to form a salt, so as to enhance the selectivity of the reduction reaction.

Preferably, according to the present disclosure, in step (2), a mass ratio between ethyl acetate and the compound of formula III is 5~20:1; further preferably, the mass ratio between ethyl acetate and the compound of formula III ranges from 10~14:1. The reason of using ethyl acetate in the present invention is to facilitate separation from the aqueous phase in the post-treatment. The resulting product, i.e., the compound of the formula IV, has a greater solubility in ethyl acetate.

Preferably, according to the present disclosure, in step (2), the reducing agent is selected from the group consisting of sodium borohydride, sodium tricyanoborohydride, sodium triacetoxyborohydride, sodium tripropionyloxyborohydride, potassium borohydride, potassium tricyanoborohydride, potassium triacetoxyborohydride or potassium tripropionyloxyborohydride; the molar ratio between the reducing agent and the compound of formula III is 2.0~4.0:1.

Preferably, according to the present disclosure, in step (2), a temperature for the reduction reaction ranges from (−30)~(−10°) C. A duration for the reduction reaction ranges from 2 hours to 8 hours.

According to the present disclosure, in step (2), the method for chiral resolution is carried out according to the prior art.

Preferably, according to the present invention, in step (3), solvent b is one selected from the group consisting of water, methanol, ethanol, propanol, butanol, ethyl acetate, dichloromethane, chloroform, 1,2-dichloroethane, benzene and toluene, or a combination of two or more thereof; a mass ratio between solvent b and the compound of formula IV is 3~12:1; and a mass ratio between solvent b and the compound of formula IV is 3~6:1.

Preferably, according to the present disclosure, in step (3), base b is selected from the group consisting of sodium hydroxide, potassium hydroxide, lithium hydroxide, potassium carbonate, sodium carbonate, potassium hydrogencarbonate or sodium hydrogencarbonate, or a mixture of two or more thereof; a molar ratio between base b and the compound of the formula IV is 1.5~4.0:1.

Preferably according to the present disclosure, in step (3), the hydrolysis reaction is carried out at a temperature of 10~100° C. Preferably, the hydrolysis reaction is carried out at a temperature of 20~50° C. A duration for the hydrolysis reaction ranges from 2 hours to 7 hours.

Preferably, according to the present invention, in step (4), solvent c is selected from the group consisting of dichloromethane, 1,2-dichloroethane, trichloromethane, tetrachloromethane, acetonitrile, tetrahydrofuran, 2-methyltetrahydrofuran, methoxycyclopentane, and methylbenzene, or a combination of two or more thereof; a mass ratio between solvent c and the compound of the formula V is 4~30:1; preferably, the mass ratio between solvent c and the compound of the formula V is 18~30:1.

Preferably, according to the present disclosure, in step (4), base c is selected from the group consisting of trimethylamine, triethylamine, tri-n-butylamine, diisopropylethylamine, potassium carbonate, sodium carbonate or calcium carbonate, or a combination of two or more thereof; a molar ratio between base c and the compound of formula V is 3.0~8.0:1.

Preferably, according to the present disclosure, the catalyst in step (4) is selected from the group consisting of N,N-dimethylformamide, pyridine or 4-dimethylaminopyridine, or a combination of two or more thereof; a mass of the catalyst is 0.1~5.0% of the mass of the compound of the formula V.

Preferably, according to the present disclosure, in step (4), a molar ratio between solid phosgene/diphosgene/phosgene and the compound of formula V is 0.6~5.0:1; preferably, a molar ratio between solid phosgene and the compound of formula V is 1.2~2.0:1; a molar ratio between diphosgene and the compound of formula V is 1.0~2.5:1, and a molar ratio between phosgene and the compound of formula V is 2.0~4.0:1.

Preferably, according to the present disclosure, the ammonia in step (4) uses one from the group consisting of ammonia gas, alcoholic solution of ammonia gas, tetrahydrofuran solution of ammonia gas, acetonitrile solution of ammonia gas, or ammonium hydroxide; a mass concentration of ammonia gas in the alcoholic solution of ammonia gas, tetrahydrofuran solution of ammonia gas, the acetonitrile solution of ammonia gas, or the ammonium hydroxide is 5~20%.

Preferably, according to the present disclosure, a molar ratio between the ammonia and the compound of formula V in step (4) is 1.0~6.0:1.

Preferably, according to the present disclosure, the reaction temperatures for the urea cyclization, acyl chlorination, amidation all range from −20° C. to 60° C.; preferably, the reaction temperatures for the urea cyclization, acyl chlorination, amidation all range from 10° C. to 30° C. Durations for the urea cyclization, acyl chlorination, amidation all range from 1 hour to 8 hours.

Preferably, according to the present invention, in step (5), solvent d is one selected from the group consisting of water, isopropanol, isobutanol, ethyl acetate, dichloromethane, chloroform, 1,2-dichloroethane or isobutyl methyl ketone, or a combination of two or more thereof; a mass ratio between solvent d and the compound of formula VI is 4~20:1; preferably, the mass ratio between solvent d and the compound of formula VI is 4~8:1.

Preferably, according to the present disclosure, in step (5), base d is selected from the group consisting of trimethylamine, triethylamine, tri-n-butylamine and diisopropylethylamine; a molar ratio between base d and the compound of formula VI is 0.2~0.7:1.

Preferably, according to the present disclosure, in step (5), when PG in the compound of formula VI is a non-silicon protecting group, the deprotecting agent is selected from the group consisting of sulfur trioxide trimethylamine complex, sulfur trioxide triethylamine complex and sulfur trioxide pyridine complex; when PG in the compound of formula VI is a silicon-containing protecting group, the deprotecting agent is fluorotetrabutylammonium; a molar ratio between the deprotecting agent and the compound of formula VI is 1.0~3.0:1.

Preferably, according to the present disclosure, in step (5), the reagent used in the sulfation is one selected from the group consisting of sulfur trioxide trimethylamine complex, sulfur trioxide triethylamine complex or sulfur trioxide pyridine complex; a molar ratio between the reagent used for sulfation and the compound of formula VI is 1.0~3.0:1.

Preferably, according to the present disclosure, in step (5), the salt forming reagent used in the tetrabutylammonium salt formation reaction is tetrabutylammonium acetate or fluorotetrabutylammonium; and a molar ratio between the salt forming reagent used in the tetrabutylammonium salt formation reaction and the compound of formula VI is 0.5~2:1.

Preferably, according to the present disclosure, in step (5), the deprotection, sulfation, and tetrabutylammonium salt formation reaction are carried out in a "one-pot" process; the reaction temperature ranges from 0° C. to 60° C.; preferably, the reaction temperature ranges from 10° C. to 30° C. Durations for the deprotection, sulfation, and tetrabutylammonium salt formation reaction all range from 1 hour to 8 hours.

Preferably, according to the present disclosure, in step (6), the reagent used in the ion exchange is sodium iso-octoate; a molar ratio between the reagent used in the ion exchange and the compound of formula VII is 1.5~3.0:1.

Preferably, according to the present disclosure, in step (6), the temperature for the ion exchange reaction ranges from 0° C. to 50° C.; preferably, the reaction temperature for the ion exchange ranges from 10° C. to 40° C. A duration for the ion exchange reaction ranges from 1 hour to 5 hours.

According to the present disclosure, in step (6), the method for the ion exchange is carried out according to the prior art.

In the present invention, piperidine-5-one-2S-carboxylate II as the raw material is subjected to condensation reaction with O-protecting hydroxylamine hydrochloride in the presence of a basic reagent to prepare the compound of formula III, 5-substituted oxyiminopiperidine-2S-carboxylate; the compound of formula III is subjected to reduction and chiral resolution to obtain the compound of formula IV, 5R-substituted oxyaminopiperidine-2S-carboxylate oxalate; the compound of formula IV is hydrolyzed in the basic condition to obtain the compound of formula V, 5R-substituted oxyaminopiperidine-2S-carboxylic acid; in the presence of a solvent, a base, and catalyst, the compound of formula V and with phosgene, solid phosgene or diphosgene are subjected to urea cyclization, acyl chlorination, and amidation in a "one-pot" process, obtaining the compound of formula VI: (2S,5R)-6-substituted oxy-7-oxo-1,6-diazabicyclo[3.2.1]octane-2-carboxamide; the compound of the formula VI is subjected to deprotection, sulfation, and tetrabutylammonium salt formation reaction to obtain the compound of formula VII, (2S,5R)-2-carbamoyl-7-oxo-1,6-diazabicyclo[3.2.1]octan-6-yl]oxy}sulfonyl tetra-n-butyl ammonium salt; and the compound of formula VII is subjected to ion exchange to prepare avibactam (I). The scheme is provided below:

Scheme 5

Technical Characteristics and Beneficial Effects of the Present Application:

1. The present invention uses the O-non-benzyl protecting hydroxylamine hydrochloride, and the resulting intermediate (2S,5R)-6-substituted oxy-7-oxo-1,6-diazabicyclo[3.2.1]octane-2-carboxamide is subjected to deprotection, sulfation, tetrabutylammonium salt formation in an acetic environment by the "one-pot" process, such that the steps are simple; besides, the protecting reagent and the sulfating reagent may use the same kind of reagent, which further reduces the cost; the present invention uses a simple method of removing the non-benzyl protecting group, without a need of using expensive trimethyl sulfoxide iodide, 9-fluorenylmethyl chloroformate (FMOC-CI), carbonyl diimidazole and 10% palladium on carbon as used in prior processes, which thus reduces residues of heavy metals, improves product quality, and further lowers the cost.

2. In the preparing process of the present disclosure, in step (2) concentrated sulfur with a specific concentration is combined with the substrate to form salt, which facilitates the selectivity of the reduction reaction. In the preparing process of the present disclosure, the step (4) is completed by the designed "one-pot" process, i.e., urea cyclization—acyl chlorination—amidation in "one-pot", such that the step is simple, which avoids the issues in conventional processes, such as complex post-amidation treatment, use of expensive protecting reagent in urea cyclization, and poor atomic economy of the reactions.

3. Compared with the conventional processes of preparing avibactam, the present process of preparing avibactam has simple preparing steps, simple schemes, ease of operation, and inexpensive starting materials; besides, the present invention does not need the expensive palladium-on-carbon catalyst, such that it has a low cost; further, it discharges less waste water, waste gas, and waste residuals, such that it is environment friendly; the yields of its respective steps are high, which facilitates industrial production of avibactam.

DETAILED DESCRIPTION OF EMBODIMENTS

Hereinafter, the present invention will be described in detail with reference to the examples, while the present invention is not limited thereto.

The percentages (%) in the examples all refer to mass percentages, unless otherwise indicated.

The raw materials piperidine-5-one-2S-carboxylate, methoxymethylhydroxylamine hydrochloride, tert-butyldimethylsilyl hydroxylamine hydrochloride are commercially available (sold by Jinan Qinsi Pharmaceutical Company).

The reaction process and product purity are monitored by a gas chromatograph or a liquid chromatograph. A liquid chromatograph equipped with a chiral column (ES-OVS, 150 mm×4.6 mm, Agilent) is used to detect the optical purity (area ratio %) and calculate the yield and e.e % value.

Example 1: Preparation of Avibactam (I)

Step (1) Preparation of
5-methoxymethyloxyiminopiperidine-2S-carboxylate
($III_1$)

To a 500 ml 4-neck flask equipped with a stirrer, a thermometer, and a reflux condenser, 200 g of 1, 2-dichloromethane, 23.5 g (0.15 mol) of methyl piperidine-5-one-2S-carboxylate, 20.5 g (0.18 mol) of methoxymethylhydroxylamine hydrochloride, and 25 g of triethylamine were separately added, then stirred for reaction at 40° C. to 45° C. for 4 hours. After the mixture was cooled to 20° C.-25° C., 100 g of water was added. Then, the solution was separated and the aqueous layer was extracted twice by 1,2-dichloroethane (50 g each). The organic phases were combined and washed twice with saturated saline (25 g each). The organic phase was distilled to recover the solvent and then distilled at a reduced pressure to obtain 31.3 g of methyl 5-methoxymethyloxyiminopiperidine-2S-carboxylate as yellowish liquid in a GC purity of 99.8% and a yield of 96.5%.

Step (2): Preparation of methyl
5R-methoxymethyloxyaminopiperidine-2S-carboxylate
oxalate ($IV_1$)

To a 500 ml 4-neck flask equipped with a stirrer and a thermometer, 200 g of ethyl acetate, 17.3 g (0.08 mol) of methyl 5-methoxymethyloxyiminopiperidine-2S-carboxylate prepared in step (1) was added and then cooled. Then, 40.3 g (0.4 mol) of concentrated sulfuric acid (mass concentration of 98%) was added dropwise at −20° C. and then stirred for 1 hour. 38.0 g (0.18 mol) of triacetoxyborohydride was added at −20° C., then stirred to react at −20° C. to −15° C. for 5 hours. The mixture was kept at a temperature below 10° C., and then the reaction mixture was slowly added into 200 g of 10% aqueous ammonia; the solution was then separated and an organic phase was washed twice by saturated saline (25 g each). The organic phase was concentrated to recover the solvent, then 80 g of ethyl acetate, 40 g of methanol, and 11.5 g (0.09 mol) of oxalic acid dihydrate were added to the residual and heated to 45° C., stirred for 1 hour, and then cooled and filtered. The obtained filter cake was first washed with a mixed liquid of 60 g of ethyl acetate/methanol (2:1) and then washed with 50 g of ethyl acetate. After drying under vacuum, 15.8 g of optical isomer methyl 5R-methoxymethyloxyaminopiperidine-2S-carboxylate oxalate was obtained in a chiral HPLC purity of 99.7% and a yield of 64.0%.

Figure 1:
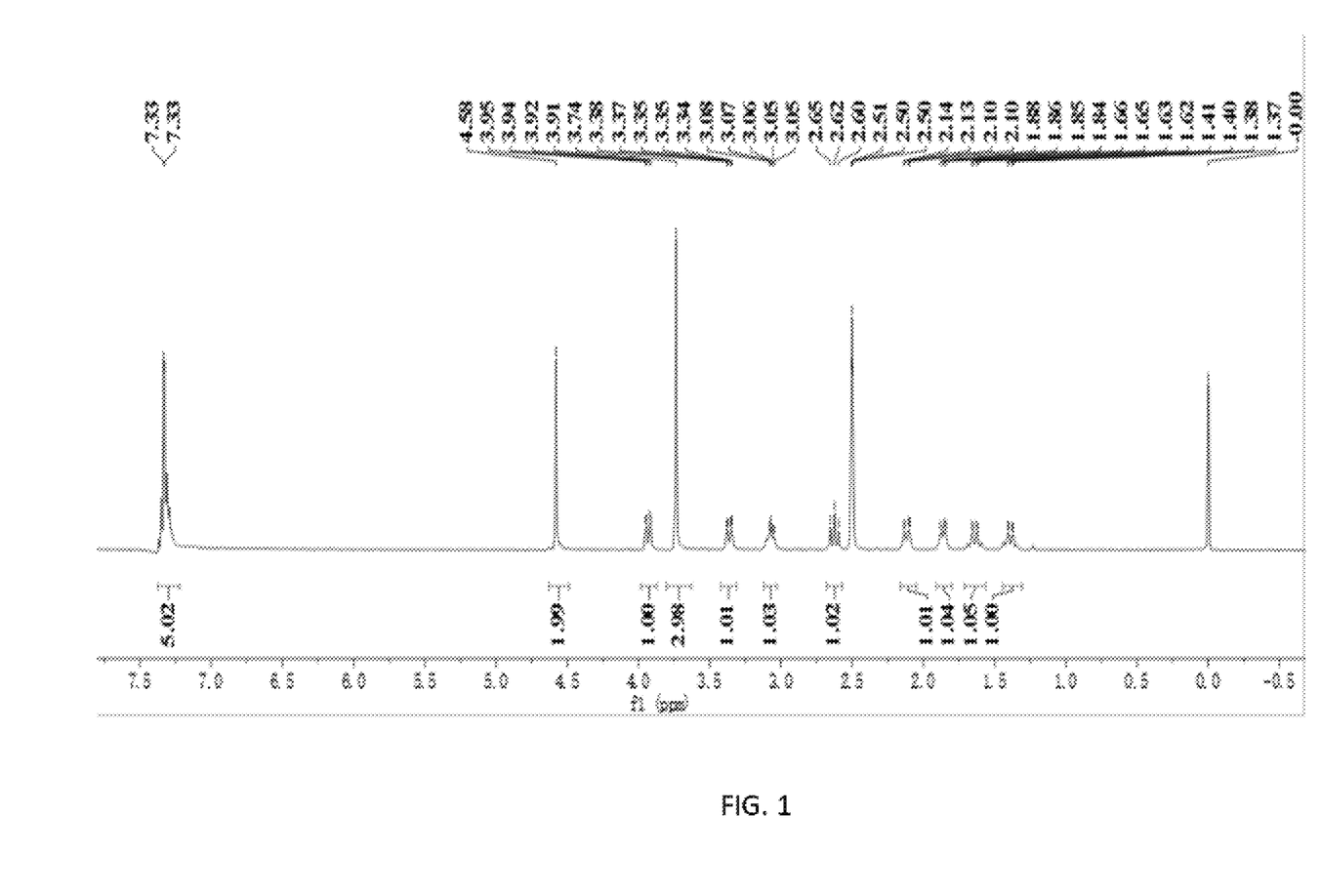
FIG. 1 shows the $^1$H-NMR spectroscopy of methyl 5R-methoxymethyloxyaminopiperidine-2S-carboxylate oxalate ($IV_1$) obtained from step (2) of example 1.

The NMR data of the product are provided below:
$^1$H-NMR (400 MHz, DMSO-d6) δ: 1.39 (m, 1H), 1.64 (m, 1H), 1.85 (m, 1H), 2.12 (m, 1H), 2.62 (t, 1H), 3.06 (m, 1H), 3.36 (d, 1H), 3.74 (s, 3H), 3.93 (q, 1H), 4.58 (s, 2H), 7.26-7.38 (m, 5H).

The $^1$H-NMR spectroscopy of the product is shown in FIG. 1.

Step (3): Preparation of
5R-methoxymethyloxyaminopiperidine-2S-carboxylic
acid ($V_1$)

To a 500 ml 4-neck flask equipped with a stirrer and a thermometer, 30.8 g (0.1 mol) of methyl 5R-methoxymethyloxyaminopiperidine-2S-carboxylate oxalate prepared in step (2), 50 g of water, 100 g of menthol, and 70 g (0.35 mol) of sodium hydroxide aqueous solution (20 wt %) were added and stirred for reaction at 30° C. to 35° C. for 3 hours. After completion of the hydrolysis reaction, the solution was cooled to 0° C. to 5° C., and then acidified with acetic acid to adjust the pH value to 3.5~3.0. The reaction mixture was filtered and dried to obtain 18.6 g of 5R-methoxymethyl-oxyaminopiperidine-2S-carboxylic acid in an HPLC purity of 99.8% and a yield of 91.2%.

Figure 2:
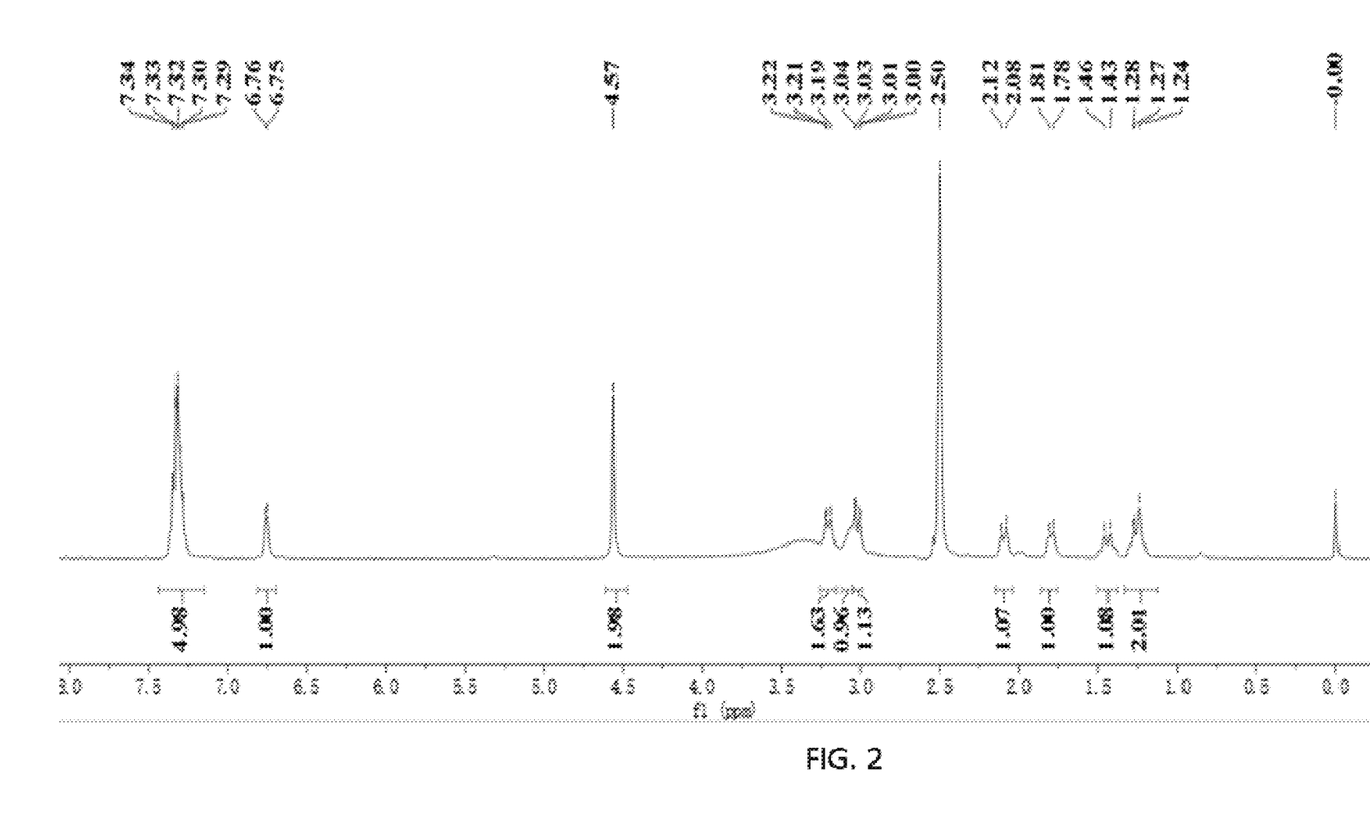
FIG. 2 shows the $^1$H-NMR spectroscopy of 5R-methoxymethyloxyaminopiperidine-2S-carboxylic acid ($V_1$) obtained from step (3) of example 1.

The NMR data of the product are provided below:
$^1$H-NMR (400 MHz, DMSO-d6) δ: 1.25 (m, 1H), 1.44 (m, 1H), 1.79 (m, 1H), 2.10 (m, 1H), 3.02 (m, 1H), 3.07 (br, 1H), 3.21 (d, 1H), 4.57 (s, 2H), 6.75 (s, 1H), 7.29-7.34 (m, 5H).

The $^1$H-NMR spectroscopy of the product is shown in FIG. 2.

Step (4): Preparation of (2S,5R)-6-methoxymethyl-oxy-7-oxo-1,6-diazabicyclo[3.2.1]octane-2-carbox-amide (VI$_1$)

To a 500 ml 4-neck flask equipped with a stirrer and a thermometer, 200 g of tetrahydrofuran, 10.2 g (0.05 mol) of 5-methoxymethyloxyaminopiperidine-2S-carboxylic acid prepared in step (3), 50 g of diisopropylethylamine, and 0.1 g of N, N-dimethylformamide were added and then cooled; a mixed solution of 23.8 g (0.08 mol) of solid phosgene and 80 g of tetrahydrofuran were added dropwise at −10° C. to 0° C., and after completion of the dropwise adding, the reaction mixture was stirred for reaction at 10° C. to 20° C. for 4 hours. 4.0~4.5 g of ammonia gas was introduced at 10° C. to 20° C. and stirred for reaction at 15° C. to 20° C. for 3 hours. The reaction liquid was poured into 300 g of ice-water mixture and separated, and then the aqueous phase was extracted twice by dichloromethane (50 g each). The organic phases were combined and washed twice by a saturated solution of sodium chloride (20 g each). After the solvent was recovered from the obtained organic phase, 10.7 g of (2S,5R)-6-methoxymethyloxy-7-oxo-1,6-diazabicyclo[3.2.1]octane-2-carboxamide was obtained in HPLC purity of 99.8% and a yield of 93.5%. Melting Point: 169.1° C.-170.0° C. Specific Rotation: [α]20 D=−26.2° (c=0.5, MeOH).

Figure 3:
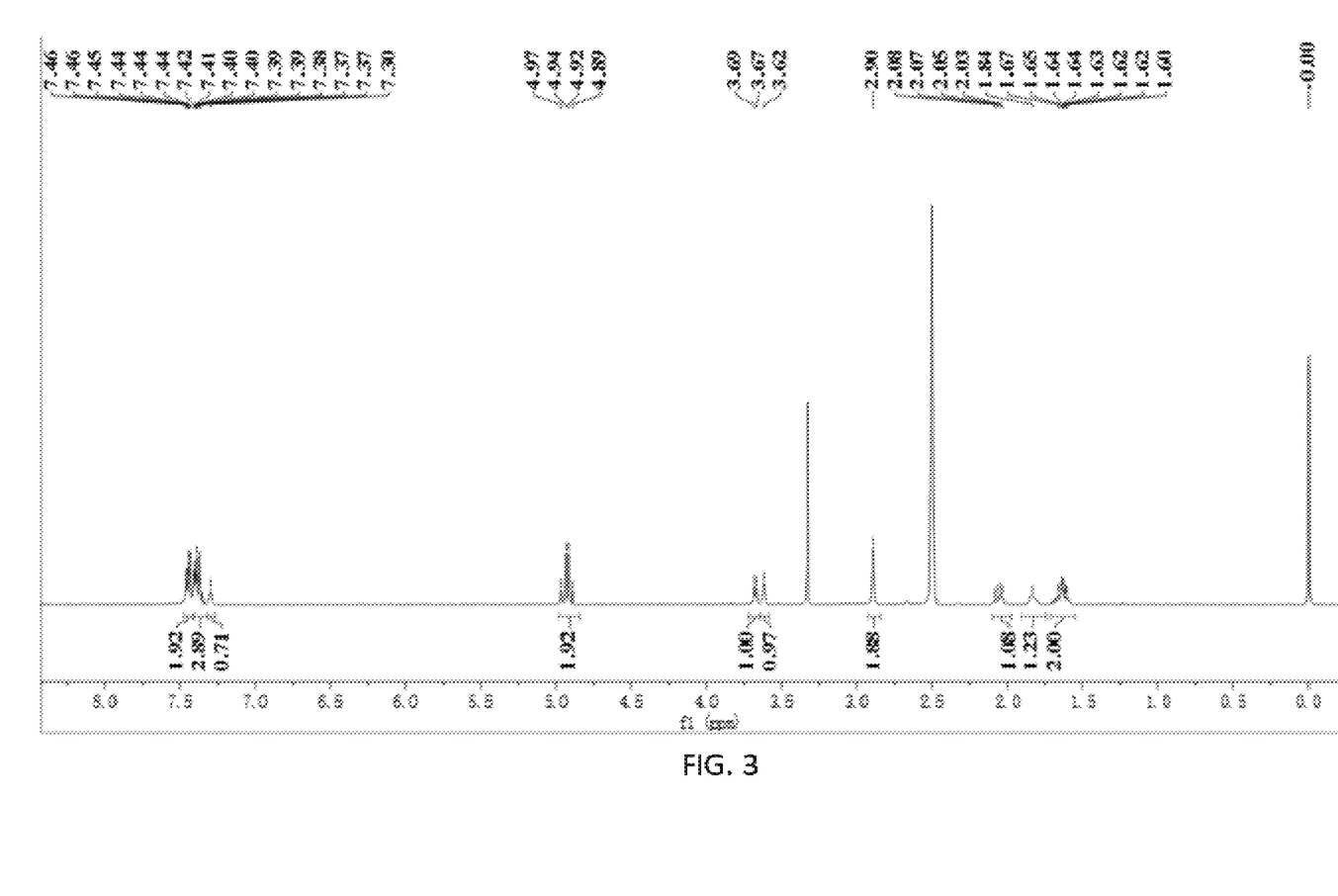
FIG. 3 is the $^1$H-NMR spectroscopy of (2S,5R)-6-methoxymethyloxy-7-oxo-1,6-diazabicyclo[3.2.1]octane-2-carboxamide ($VI_1$) obtained from step (4) of example 1.

The NMR data of the product are provided below:
$^1$H-NMR (400 MHz, DMSO-d6) δ: 1.63 (m, 2H), 1.84 (m, 1H), 2.06 (m, 1H), 2.90 (s, 2H), 3.62 (br, 1H), 3.68 (d, 1H), 4.94 (q, 1H), 4.58 (s, 2H), 7.28-7.46 (m, 5H).

The $^1$H-NMR spectroscopy of the product is shown in FIG. 3.

Step (5): Preparation of {(2S,5R)-2-carbamoyl-7-oxo-1,6-diazabicyclo[3.2.1]octan-6-yl]oxy}sulfonyl tetra-n-butyl ammonium salt (VII)

To a 500 ml 4-neck flask equipped with a stirrer and a thermometer, 100 g of isopropanol, 2.0 g of water, 23.0 g (0.1 mol) of (2S,5R)-6-methoxymethyloxy-7-oxo-1,6-diazabicyclo[3.2.1]octane-2-carboxamide prepared in step (4), 5.0 g of triethylamine, and 36.0 g (0.12 mol) of tetrabutylammonium acetate were added, and 46.5 g (0.25 mol) of sulfur trioxide trimethylamine complex was added at 10° C. to 15° C.; the mixture solution was stirred for reaction at 15° C. to 20° C. for 4 hours. The reaction liquid was poured into 150 g of dichloromethane and 150 g of ice-water mixture. Acetic acid was then added to adjust the system pH value to 3.5~2.5. The mixed solution was separated and then the aqueous layer was extracted twice by dichloromethane (50 g each). The organic phases were combined and washed twice by a saturated solution of sodium chloride (20 g each). After the solvent was recovered from the obtained organic phase, the residues were recrystallized by 50 g of dichloromethane-methyl isobutyl ketone (volume ratio 1:3) to obtain 46.3 g of {[(2S,5R)-2-carbamoyl-7-oxo-1,6-diazabicyclo[3.2.1]octan-6-yl]oxy}sulfonyl tetra-n-butyl ammonium salt in HPLC purity of 99.9% and a yield of 91.5%. Specific Rotation: [α]20 D=−29.4 (c=0.5, H2O).

Figure 4:
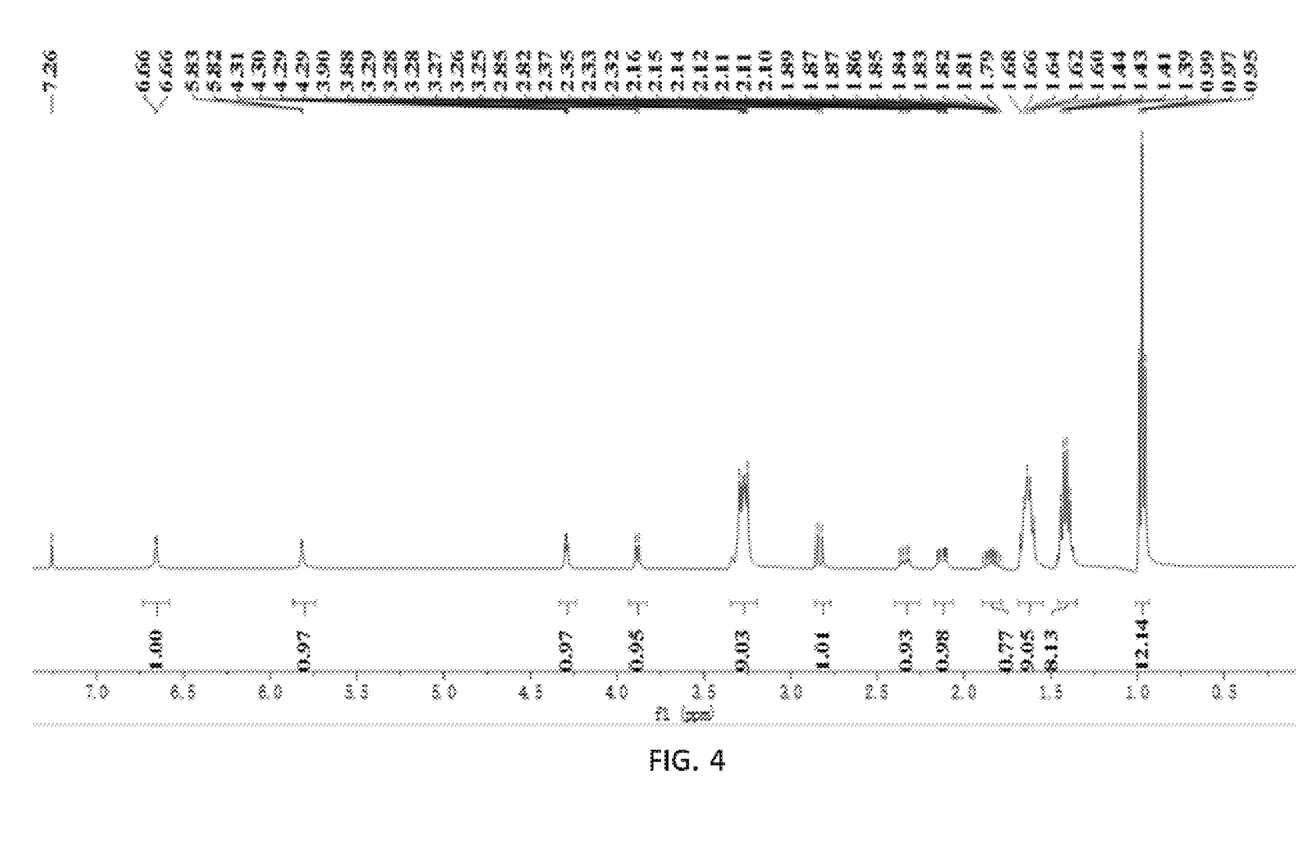
FIG. 4 is the $^1$H-NMR spectroscopy of {[(2S,5R)-2-carbamoyl-7-oxo-1,6-diazabicyclo[3.2.1]octan-6-yl]oxy}sulfonyl tetra-n-butyl ammonium salt (VII) obtained from step (5) of example 1.

The NMR data of the product are provided below:
$^1$H-NMR (400 MHz, DMSO-d6) δ: 0.97 (t, 12H), 1.42 (m, 8H), 1.64 (m, 9H), 1.84 (m, 1H), 2.12 (m, 1H), 2.35 (m, 1H), 2.83 (d, 1H), 3.27 (m, 9H), 3.89 (d, 1H), 4.30 (s, 1H), 5.83 (s, 1H), 6.66 (s, 1H).

The $^1$H-NMR spectroscopy of the product is shown in FIG. 4.

Step (6): Preparation of Avibactam (I)

To a 500 ml flask equipped with a stirrer and a thermometer, 260 g of ethyl alcohol (2 wt % of water), 56.0 g (0.1 mol) of {[(2S,5R)-2-carbamoyl-7-oxo-1,6-diazabicyclo[3.2.1]octan-6-yl]oxy}sulfonyl tetra-n-butyl ammonium salt was added, stirred and dissolved at 20° C. to 25° C.

33.2 g (0.2 mol) of sodium iso-octoate was dissolved in advance in 280.0 g of ethyl alcohol to prepare a solution. The solution was added dropwise into the system at 20° C. to 25° C.; a white solid was precipitated; after completion of dropwise adding, the solution was stirred at 20° C. to 25° C. for 3 hours. The mixed solution was filtered, and washed with 100.0 g of ethyl alcohol, obtaining 26.2 g of avibactam (I) in HPLC purity of 99.9% and a yield of 91.5%. Specific Rotation: [α]20 D=−54.4° (c=0.5, H2O).

Figure 5:
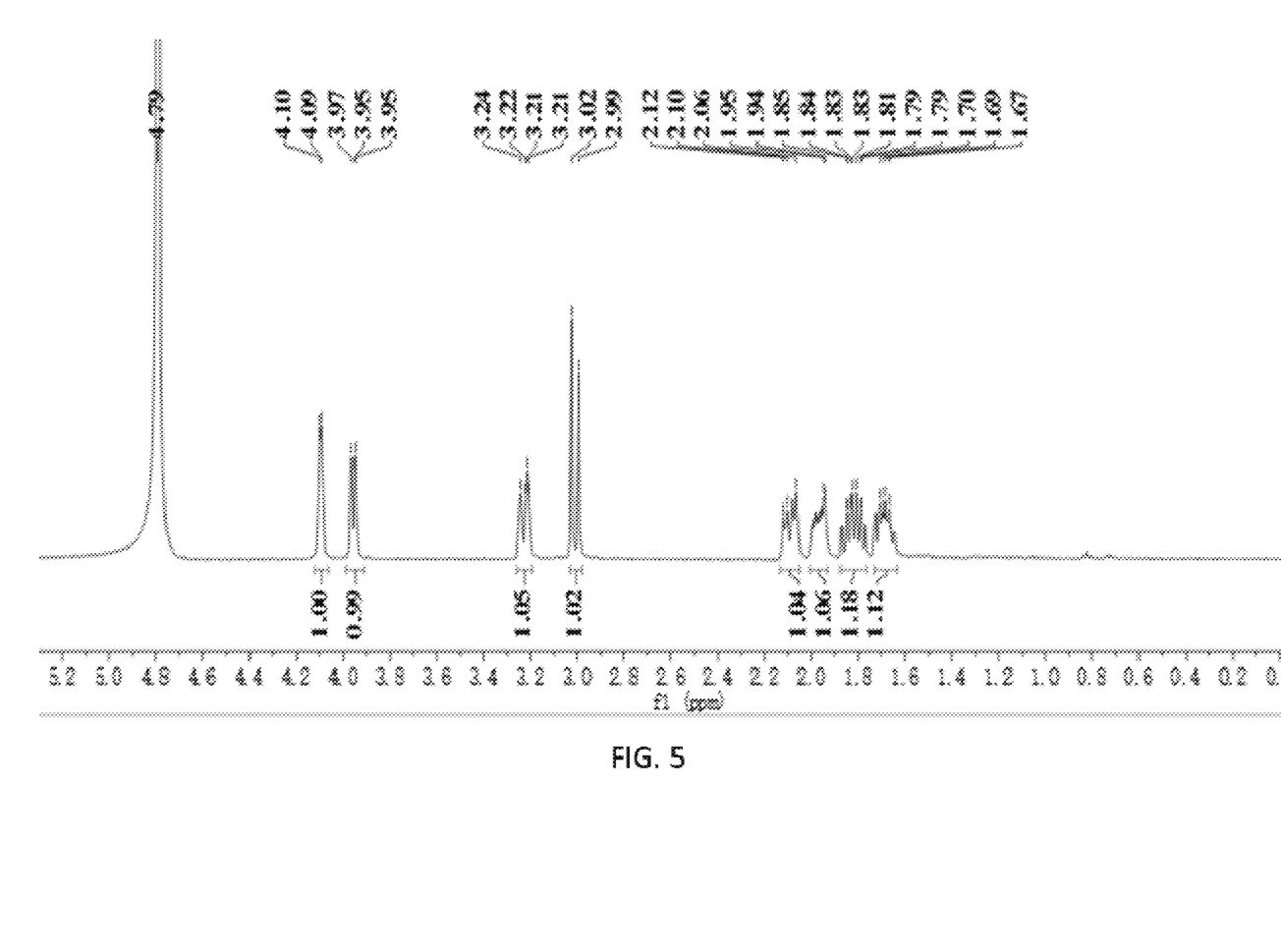
FIG. 5 is the $^1$H-NMR spectroscopy of avibactam (I) obtained from step (6) of example 1.

The NMR data of the product are provided below:
$^1$H-NMR (400 MHz, D2O) δ: 1.69 (m, 1H), 1.83 (m, 1H), 1.96 (m, 1H), 2.10 (m, 1H), 3.00 (d, 1H), 3.22 (d, 1H), 3.96 (d, 1H), 4.09 (q, 1H).

Figure 6:
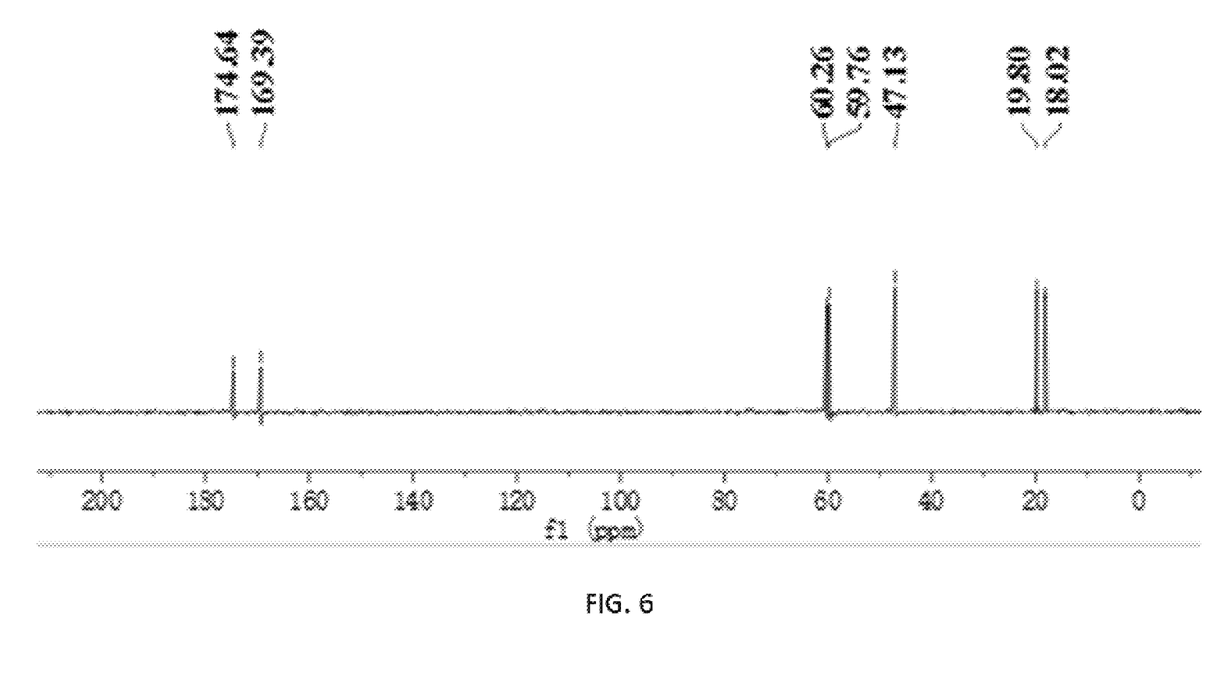
FIG. 6 is the $^{13}$C-NMR spectroscopy of avibactam (I) obtained from step (6) of example 1.

$^{13}$C-NMR (400 MHz, D2O) δ: 174.64, 169.39, 60.26, 59.76, 47.13, 19.80, 18.02.

The $^1$H-NMR spectroscopy of the product is shown in FIG. 5, and the $^{13}$C-NMR spectroscopy of the product is shown in FIG. 6.

Example 2: Preparation of Avibactam (I)

Step (1) Preparation of methyl 5-tert-butyldimethyl-silyloxyiminopiperidine-2S-carboxylate (III$_2$)

To a 500 ml 4-neck flask equipped with a stirrer, a thermometer, and a reflex condenser, 200 g of dichloromethane, 23.5 g (0.15 mol) of methyl piperidine-5-one-2S-carboxylate, 36.5 g (0.2 mol) of tert-butyldimethylsilylhydroxylamine hydrochloride, and 25 g of triethylamine were separately added, then stirred for reaction at 38° C. to 40° C. for 5 hours. After the mixture was cooled to 20° C.-25° C., 100 g of water was added. Then, the solution was separated and an aqueous layer was extracted twice by dichloromethane (50 g each). The organic phases were combined and washed twice by saturated saline (25 g each). The organic phase was distilled to recover the solvent and then distilled at a reduced pressure to obtain 41.0 g of methyl 5-tert-butyldimethylsilyloxyiminopiperidine-2S-carboxylate as yellowish liquid in a GC purity of 99.9% and a yield of 95.6%.

Step (2): Preparation of methyl 5R-tert-butyldimethylsilyloxyaminopiperidine-2S-carboxylate oxalate (IV$_2$)

To a 500 ml 4-neck flask equipped with a stirrer and a thermometer, 250 g of ethyl acetate, 22.9 g (0.08 mol) of methyl 5-tert-butyldimethylsilyloxyiminopiperidine-2S-carboxylate prepared in step (1) was added and then cooled. Then, 40.3 g (0.4 mol) of concentrated sulfuric acid (mass concentration of 98%) was added dropwise at −20° C. and then stirred for 1 hour after completion of dropwise adding. 38.0 g (0.18 mol) of sodium triacetoxy borohydride was added at −20° C., and then stirred to react at −20° C. to −15° C. for 5 hours. The mixture was kept at a temperature below 10° C., and then the reaction mixture was slowly added into 200 g of 10% aqueous ammonia; the solution was then separated and an organic phase was washed twice by saturated saline (25 g each). The organic phase was concentrated to recover the solvent, then 80 g of ethyl acetate, 40 g of methanol, and 11.5 g (0.09 mol) of oxalic acid dihydrate were added to the residual and heated to 45° C., stirred for 1 hour, and then cooled and filtered. The obtained filter cake was first washed with a mixed liquid of 60 g of ethyl acetate/methanol (2:1) and then washed with 50 g of ethyl acetate. After drying under vacuum, 19.7 g of optical isomer methyl 5-tert-butyldimethylsilyloxyaminopiperidine-2S-carboxylate oxalate was obtained in a chiral HPLC purity of 99.8% and a yield of 65.3%.

Step (3) Preparation of 5R-tert-butyldimethylsilyloxyaminopiperidine-2S-carboxylic acid (V$_1$)

To a 500 ml 4-neck flask equipped with a stirrer and a thermometer, 37.8 g (0.1 mol) of methyl tert-butyldimethylsilyloxyaminopiperidine-2S-carboxylate oxalate prepared in step (2), 50 g of water, 100 g of ethyl alcohol, and 70 g (0.35 mol) of sodium hydroxide aqueous solution (20 wt %) were added and stirred for reaction at 20° C. to 25° C. for 4 hours. After completion of the hydrolysis reaction, the solution was cooled to 0° C. to 5° C., and then acidified with acetic acid to adjust the pH value to 3.5~3.0. The reaction mixture was filtered and dried to obtain 25.3 g of 5R-tert-butyldimethylsilyloxyaminopiperidine-2S-carboxylic acid in HPLC purity of 99.9% and a yield of 92.3%.

Step (4): Preparation of (2S,5R)-6-tert-butyldimethylsilyloxy-7-oxo-1,6-diazabicyclo[3.2.1]octane-2-carboxamide (VI$_2$)

To a 500 ml 4-neck flask equipped with a stirrer and a thermometer, 200 g of acetonitrile, 13.7 g (0.05 mol) of 5-tert-butyldimethylsilyloxyaminopiperidine-2S-carboxylic acid prepared in step (3), 45 g of diisopropylethylamine, and 0.1 g of N, N-dimethylformamide were added and then cooled; a mixed solution of 23.8 g (0.12 mol) of diphosgene and 80 g of acetonitrile were added dropwise at −10° C. to 0° C., and after completion of the dropwise adding, the reaction mixture was stirred for reaction at 10° C. to 20° C. for 4 hours. 40 g (10 wt %) of ammonia-acetonitrile solution was added dropwise at 10° C. to 20° C. and stirred at 15° C. to 20° C. for reaction for 4 hours; the reaction liquid was poured into the 300 g of ice-water mixture. The mixed solution was separated and the aqueous layer was extracted twice with dichloromethane (50 g each). The organic phases were combined and washed twice by a saturated solution of sodium chloride (20 g each). After the solvent was recovered from the obtained organic phase, 13.8 g of (2S,5R)-6-tert-butyldimethylsilyloxy-7-oxo-1,6-diazabicyclo[3.2.1]octane-2-carboxamide was obtained in HPLC purity of 99.9% and a yield of 92.1%.

Step (5): Preparation of {[(2S,5R)-2-carbamoyl-7-oxo-1,6-diazabicyclo[3.2.1]octan-6-yl]oxy}sulfonyl tetra-n-butyl ammonium salt (VII)

To a 500 ml 4-neck flask equipped with a stirrer and a thermometer, 120 g of isopropanol, 2.0 g of water, 30.0 g (0.1 mol) of (2S,5R)-6-tert-butyldimethylsilyloxy-7-oxo-1,6-diazabicyclo[3.2.1]octane-2-carboxamide prepared in step (4), 5.5 g of triethylamine, and 39.0 g (0.15 mol) of fluorotetrabutylammonium were added, and 22.5 g (0.12 mol) of sulfur trioxide trimethylamine complex was added at 10° C. to 15° C.; the mixture solution was stirred for reaction at 15° C. to 20° C. for 5 hours. The reaction liquid was poured into 150 g of dichloromethane and 100 g of ice-water mixture. Acetic acid was then added to adjust the system pH value to 3.5~2.5. The mixed solution was separated and then the aqueous layer was extracted twice by dichloromethane (50 g each). The organic phases were combined and washed twice by a saturated solution of sodium chloride (20 g each). After the solvent was recovered from the obtained organic phase, the residues were recrystallized by 50 g of dichloromethane-methyl isobutyl ketone (volume ratio 1:3) to obtain 47.1 g of {[(2S,5R)-2-carbamoyl-7-oxo-1,6-diazabicyclo[3.2.1]octan-6-yl]oxy}sulfonyl tetra-n-butyl ammonium salt in HPLC purity of 99.9% and a yield of 93.1%.

Step (6): Preparation of Avibactam (I)

To a 500 ml flask equipped with a stirrer and a thermometer, 260 g of 98% ethyl alcohol (2 wt % of water), 50.6 g (0.1 mol) of {[(2S,5R)-2-carbamoyl-7-oxo-1,6-diazabicyclo[3.2.1]octan-6-yl]oxy}sulfonyl tetra-n-butyl ammonium salt was added, and the mixture was stirred and dissolved at 20° C. to 30° C.

Additionally, 33.2 g (0.2 mol) of sodium iso-octoate was dissolved in 280.0 g of ethyl alcohol to prepare a solution. The solution was added dropwise into the system at 20° C. to 30° C.; a white solid was precipitated; after completion of dropwise adding, the solution was stirred at 20° C. to 30° C. for 3 hours. The mixed solution was filtered, and washed with 100.0 g of ethyl alcohol, obtaining 25.9 g of avibactam (I) in HPLC purity of 99.8% and a yield of 90.2%.

Comparative Example 1

A process for preparing avibactam comprises the following steps.

Step (1) Preparation of methyl 5-methoxymethyloxyiminopiperidine-2S-carboxylate (III$_1$)

This step differed from step (1) of Example 1 in that:
the condition for the condensation reaction in this step was to stir for reaction at 20° C. to 25° C. for 8 hours.
The remaining conditions were consistent with Example 1.
24.5 g of methyl 5-methoxymethyloxyiminopiperidine-2S-carboxylate as yellowish liquid in a GC purity of 99.2% and a yield of 75.5% was obtained.
It is seen that the temperature for condensation reaction has a significant impact on the yield of the target product.

Step (2): Preparation of methyl 5R-methoxymethyloxyaminopiperidine-2S-carboxylate oxalate (IV₁)

This step differed from step (2) of Example 1 in that:
the amount of concentrated sulfur acid (98% mass concentration) was 20.0 g (0.2 mol);
38.0 g (0.18 mol) of sodium triacetoxyborohydride was added at −20° C., and then the mixture was stirred to react at −20° C. to −15° C. for 5 hours. The mixture was kept at a temperature below 10° C., and then the reaction mixture was slowly added into 100 g of 10% aqueous ammonia.
The remaining conditions were consistent with Example 1.
8.8 g of optical isomer methyl 5R-methoxymethyloxyaminopiperidine-2S-carboxylate oxalate in a chiral HPLC purity of 98.3% and a yield of 35.5% was obtained.
It is seen that amount of the concentrated sulfuric acid affects the selectivity of the reduction reaction, which has a relatively significant impact on the yield and purity of the product.

Step (3): Preparation of 5R-methoxymethyloxyaminopiperidine-2S-carboxylic acid (V₁)

This step differed from step (3) of Example 1 in that:
the condition for the hydrolysis reaction was to stir for reaction at 70° C. to 75° C. for 3 hours.
The remaining conditions were consistent with Example 1.
17.4 g of 5R-methoxymethyloxyaminopiperidine-2S-carboxylic acid as yellowish powder in HPLC purity of 98.6% in HPLC and a yield of 85.5% was obtained.

Step (4): Preparation of (2S,5R)-6-methoxymethyloxy-7-oxo-1,6-diazabicyclo[3.2.1]octane-2-carboxamide (VI₁)

This step differed from step (4) of Example 1 in that:
the amount of solid phosgene added dropwise was 14.9 g (0.05 mol).
The remaining conditions were consistent with Example 1.
9.8 g of (2S,5R)-6-methoxymethyloxy-7-oxo-1,6-diazabicyclo [3.2.1] octane-2-carboxamide in HPLC purity of 99.0% and a yield of 85.6% was obtained.

Step (5): Preparation of {(2S,5R)-2-carbamoyl-7-oxo-1,6-diazabicyclo[3.2.1]octan-6-yl]oxy}sulfonyl tetra-n-butyl ammonium salt (VII)

This step differed from step (5) of Example 1 in that:
28.0 g (0.15 mol) of sulfur trioxide trimethylamine complex was added at 32° C. to 35° C., and the mixture was stirred for reaction at 32° C. to 35° C. for 4 hours.
The remaining conditions were consistent with Example 1;
40.3 g of {[(2S,5R)-2-carbamoyl-7-oxo-1,6-diazabicyclo [3.2.1]octan-6-yl]oxy}sulfonyl tetra-n-butyl ammonium salt in HPLC purity of 99.9% and a yield of 79.6% was obtained.
It is seen that the reaction temperature for deprotection, sulfation, tetrabutylammonium salt formation has a significant impact on the yield of the product.

Step (6): Preparation of Avibactam (I)

This step differed from step (6) of Example 1 in that:
the condition for the ion exchange reaction was to stir for reaction at 40° C. to 45° C. for 3 hours.
The remaining conditions were consistent with Example 1.
26.0 g of avibactam (I) in HPLC purity of 99.1% and a yield of 90.8% was obtained.

What is claimed is:
1. A process for preparing an avibactam (I), comprising steps of:
(1) a compound of formula II is subjected to condensation reaction with O-protecting hydroxylamine hydrochloride in solvent a and under the catalysis of base a to prepare a compound of formula III:

where R in the compound of formula II is identical to R in the compound of formula III, which is one selected from the group consisting of methyl, ethyl, isopropyl, n-propyl, tert-butyl, n-butyl, isobutyl, or benzyl; PG in the compound of formula III is one selected from the group consisting of methoxymethyl, benzyloxymethyl, tert-butyldimethylsilyl, tert-butyldiphenylsilyl, triethylsilyl or triisopropylsilyl; the solvent a is one or more than one selected from the group consisting of methanol, ethanol, propanol, butanol, ethyl acetate, tetrahydrofuran, acetonitrile, dichloromethane, chloroform, 1,2-dichloroethane, benzene, and toluene; the base a is an inorganic base or an organic base; the inorganic base is one or more than one selected from the group consisting of potassium carbonate, sodium carbonate, calcium carbonate, potassium hydrogencarbonate, sodium hydrogencarbonate, calcium hydrogencarbonate, potassium acetate, sodium acetate and calcium acetate;
(2) the compound of formula III is subjected to reduction with a reducing agent in the presence of concentrated sulphuric acid and ethyl acetate and chiral resolution to obtain a compound of IV:

where R and PG in the compound of the formula IV have the same meanings as R and PG in the compound of formula III;

(3) the compound of formula IV is hydrolyzed in the presence of base b and in solvent b to obtain a compound of formula V;

where PG in the compound of the formula V has the same meaning as PG in the compound of formula IV; the solvent b is one or more selected from the group consisting of water, methanol, ethanol, propanol, butanol, ethyl acetate, dichloromethane, chloroform, 1,2-dichloroethane, benzene and toluene; the base b is one or more selected from the group consisting of sodium hydroxide, potassium hydroxide, lithium hydroxide, potassium carbonate, sodium carbonate, calcium carbonate, potassium hydrogencarbonate and sodium hydrogencarbonate;

(4) the compound of formula V is subjected to urea cyclization and acyl chlorination with phosgene, solid phosgene or diphosgene in the presence of base c and catalyst in solvent c, and then is subjected to amidation to obtain a compound of formula VI; the solvent c is selected from the group consisting of dichloromethane, 1,2-dichloroethane, trichloromethane, tetrachloromethane, acetonitrile, tetrahydrofuran, 2-methyltetrahydrofuran, methoxycyclopentane and methylbenzene; the base c is one or more selected from the group consisting of trimethylamine, triethylamine, tri-n-butylamine, diisopropylethylamine, potassium carbonate, sodium carbonate and calcium carbonate;

where PG in the compound of the formula VI has the same meaning as PG in the compound of formula V;

(5) the compound of the formula VI is subjected to deprotection with a deprotection reagent, sulfation, and tetrabutylammonium salt formation under the catalysis of base d and in solvent d to obtain the compound of the formula VII; the solvent d is one or more selected from the group consisting of water, isopropanol, isobutanol, ethyl acetate, dichloromethane, chloroform, 1,2-dichloroethane and isobutyl methyl ketone; the base d is one or more selected from the group consisting of trimethylamine, triethylamine, tri-n-butylamine and diisopropylethylamine;

(6) the compound of the formula VII is subjected to ion exchange to obtain the avibactam (I) that has the formula I shown as following:

2. A The process for preparing the avibactam (I) according to claim 1, wherein step (1) comprises one or more of conditions below:
  A. the O-protecting hydroxylamine hydrochloride is one selected from the group consisting of methoxymethyl hydroxylamine hydrochloride, benzyloxymethyl hydroxylamine hydrochloride, tert-butyldimethylsilyl hydroxylamine hydrochloride, tert-butyldiphenylsilyl hydroxylamine hydrochloride, triethylsilyl hydroxylamine hydrochlorid and triisopropylsilyl hydroxylamine hydrochloride; a molar ratio between the O-protecting hydroxylamine hydrochloride and the compound of formula II is (0.9-1.5):1;
  B. a mass ratio between the solvent a and the compound of formula II is (3-15):1;
  C. a mass ratio between the base a and the compound of formula II is (0.5-1.5):1.

3. The process for preparing the avibactam (I) according to claim 1, wherein in step (1), the temperature for the condensation reaction ranges from 30° C. to 80° C.

4. The process for preparing the avibactam (I) according to claim 1, wherein in step (2), the concentrated sulfuric acid is a sulfuric acid with a mass fraction ranging from 95% to 98%, and a molar ratio between the concentrated sulfuric acid and the compound of the formula III is (3.0-6.0):1.

5. The process for preparing the avibactam (I) according to claim 1, wherein step (2) comprises one or more of conditions below:
  A. a mass ratio between ethyl acetate and the compound of formula III is (5-20):1;
  B. the reducing agent is selected from the group consisting of sodium borohydride, sodium tricyanoborohydride, sodium triacetoxyborohydride, sodium tripropionyloxyborohydride, potassium borohydride, potassium tricyanoborohydride, potassium triacetoxyborohydride and potassium tripropionyloxyborohydride; the molar ratio between the reducing agent and the compound of formula III is (2.0-4.0):1;

C. a temperature for the reduction reaction is from (30)° C. to (10)° C.

6. The process for preparing the avibactam (I) according to claim 1, wherein step (3) comprises one or more of conditions below:
   A. a mass ratio between solvent b and the compound of formula IV is (3-12):1;
   B. a molar ratio between the base b and the compound of the formula IV is (1.5-4.0):1;
   C. the temperature for hydrolysis reaction is 10° C. to 100° C.

7. The process for preparing the avibactam (I) according to claim 1, wherein step (4) comprises one or more of conditions below:
   A. a mass ratio between the solvent c and the compound of the formula V is (4-30):1;
   B. a molar ratio between the base c and the compound of formula V is (3.0-8.0):1;
   C. the catalyst is one or more selected from the group consisting of N,N-dimethylformamide, pyridine and 4-dimethylaminopyridine; a mass of the catalyst is 0.1-5.0% of the mass of the compound of the formula V;
   D. a molar ratio between the solid phosgene/diphosgene/phosgene and the compound of formula V is (0.6-5.0):1;
   E. the ammonia is selected from the group consisting of ammonia gas, alcoholic solution of ammonia gas, tetrahydrofuran solution of ammonia gas, acetonitrile solution of ammonia gas, and ammonium hydroxide; a mass concentration of ammonia gas in the alcoholic solution of ammonia gas, tetrahydrofuran solution of ammonia gas, acetonitrile solution of ammonia gas, or ammonium hydroxide is 5-20%;
   F. a molar ratio between the ammonia and the compound of formula V is (1.0-6.0):1;
   G. the reaction temperatures of the urea cyclization, acyl chlorination, amidation is from −20° C. to 60° C.

8. The process for preparing the avibactam (I) according to claim 1, wherein step (5) comprises one or more of conditions below:
   A. a mass ratio between the solvent d and the compound of formula VI is (4-20):1;
   B. a molar ratio between the base d and the compound of formula VI is (0.2-0.7):1;
   C. when PG in the compound of formula VI is a non-silicon protecting group, the deprotecting agent is selected from the group consisting of sulfur trioxide trimethylamine complex, sulfur trioxide triethylamine complex and sulfur trioxide pyridine complex; when PG in the compound of formula VI is a silicon-containing protecting group, the deprotecting agent is fluorotetrabutylammonium; a molar ratio between the deprotecting agent and the compound of formula VI is (1.0-3.0):1;
   D. the reagent used in the sulfation is one selected from the group consisting of sulfur trioxide trimethylamine complex, sulfur trioxide triethylamine complex and sulfur trioxide pyridine complex; a molar ratio between the reagent used for sulfation and the compound of formula VI is (1.0-3.0):1;
   E. the salt forming reagent used in the tetrabutylammonium salt formation reaction is tetrabutylammonium acetate or fluorotetrabutylammonium; and a molar ratio between the salt forming reagent used in the tetrabutylammonium salt formation reaction and the compound of formula VI is (0.5-2):1.

9. The method of preparing the avibactam (I) according to claim 1, wherein in step (5), the deprotection, sulfation, and tetrabutylammonium salt formation reaction are carried out in a "one-pot" process; the reaction temperature is from 0° C. to 60° C.

10. The process for preparing the avibactam (I) according to claim 1, wherein step (6) comprises one or more of conditions below:
    A. the reagent used in the ion exchange is sodium iso-octoate; a molar ratio between the reagent used in the ion exchange and the compound of formula VII is (1.5-3.0):1;
    B. the temperature for the ion exchange reaction is from 0° C. to 50° C.

* * * * *